(12) United States Patent
Falkenberg

(10) Patent No.: US 11,298,490 B2
(45) Date of Patent: Apr. 12, 2022

(54) TRACHEOSTOMA DEVICE HOLDER

(71) Applicant: Atos Medical AB, Horby (SE)

(72) Inventor: Richard Falkenberg, Horby (SE)

(73) Assignee: Atos Medical AB

( * ) Notice: Subject to any disclaimer, the term of this patent is extended or adjusted under 35 U.S.C. 154(b) by 0 days.

(21) Appl. No.: 17/280,838

(22) PCT Filed: Sep. 26, 2019

(86) PCT No.: PCT/SE2019/050920
§ 371 (c)(1),
(2) Date: Mar. 26, 2021

(87) PCT Pub. No.: WO2020/067980
PCT Pub. Date: Apr. 2, 2020

(65) Prior Publication Data
US 2021/0308402 A1 Oct. 7, 2021

(30) Foreign Application Priority Data
Sep. 27, 2018 (SE) .................................. 1851155-0

(51) Int. Cl.
*A61M 16/04* (2006.01)
*A61M 25/02* (2006.01)

(52) U.S. Cl.
CPC . *A61M 16/0465* (2013.01); *A61M 2025/0266* (2013.01); *A61M 2205/0216* (2013.01); *A61M 2205/0238* (2013.01); *A61M 2207/00* (2013.01)

(58) Field of Classification Search
CPC .................. A61M 16/0465; A61M 2025/0266
See application file for complete search history.

(56) References Cited

U.S. PATENT DOCUMENTS 3,373,745 A * 3/1968 Benfield ................. A61F 5/443
604/338
4,054,140 A * 10/1977 Etes ....................... A61F 5/445
604/343

(Continued)

FOREIGN PATENT DOCUMENTS

EP 0674890 A2 10/1995
EP 0998247 A1 5/2000

(Continued)

OTHER PUBLICATIONS

Cured Polyurethane MSDS from Meridian Laboratory, Jun. 22, 2005 (Year: 2005).*

(Continued)

*Primary Examiner* — Kathryn E Ditmer
(74) *Attorney, Agent, or Firm* — Fishman Stewart PLLC

(57) ABSTRACT

A tracheostoma device holder for holding a tracheostoma device superimposed of a tracheostoma of a person. The tracheostoma device holder may include a plate and a tracheostoma device fitting. The plate may be configured for attachment over a tracheostoma via a proximal side thereof. The plate may include a through hole. The tracheostoma device fitting may include a through passage arranged superimposed the through hole. The tracheostoma device fitting may extend distally from the plate. The plate may further include a disc of a thermoplastic material and a plate material arranged at least laterally of the disc. The plate material may have a melting point different from a melting point of the disc.

20 Claims, 3 Drawing Sheets

(56) References Cited

U.S. PATENT DOCUMENTS

| | | | | |
|---|---|---|---|---|
| 4,325,366 | A * | 4/1982 | Tabor | A61M 16/0468 128/207.16 |
| 4,439,872 | A * | 4/1984 | Henley-Cohn | A61F 2/203 623/9 |
| 5,074,852 | A | 12/1991 | Castellana et al. | |
| 5,718,696 | A * | 2/1998 | Kollerup | A61F 5/443 604/339 |
| 2010/0324511 | A1 * | 12/2010 | Dove | A61F 5/445 604/342 |
| 2013/0138065 | A1 * | 5/2013 | Buus | A61F 5/443 604/344 |
| 2013/0213404 | A1 * | 8/2013 | Leibitzki | A61M 16/047 128/207.14 |
| 2013/0226116 | A1 * | 8/2013 | Edvardsen | A61F 5/445 604/338 |
| 2013/0226117 | A1 * | 8/2013 | Hansen | A61L 24/046 604/338 |
| 2014/0326247 | A1 * | 11/2014 | Dirven | A61M 16/0497 128/207.16 |
| 2015/0306327 | A1 * | 10/2015 | Persson | A61M 16/0497 128/200.26 |
| 2018/0235801 | A1 * | 8/2018 | Oellgaard | A61F 5/445 |
| 2020/0297524 | A1 * | 9/2020 | Hunt | A61F 5/445 |

FOREIGN PATENT DOCUMENTS

| | | | | |
|---|---|---|---|---|
| EP | 1378219 | A2 | 1/2004 | |
| EP | 1984044 | A1 | 10/2008 | |
| EP | 2547294 | A1 | 1/2013 | |
| GB | 2369591 | A | 6/2002 | |
| GB | 2517680 | A | 3/2015 | |
| WO | WO-9817212 | A1 | 4/1998 | |
| WO | WO-07092210 | A1 | 8/2007 | |
| WO | WO-2011113442 | A1 | 9/2011 | |
| WO | WO-2012163994 | A1 | 12/2012 | |
| WO | WO-2017050340 | A1 | 3/2017 | |
| WO | WO-2017059868 | A1 | 4/2017 | |
| WO | WO-2017135861 | A1 * | 8/2017 | A61M 16/047 |
| WO | WO-2017135867 | A1 * | 8/2017 | A61F 13/02 |
| WO | WO-2017167582 | A2 * | 10/2017 | A61F 5/4405 |
| WO | WO-2018009118 | A1 | 1/2018 | |

OTHER PUBLICATIONS

Generic SEC properties, accessed at https://plastics.ulprospector.com/generics/53/c/t/thermoplastic-elastomer-tpe-properties-processing/sp/18 on Aug. 3, 2021 (Year: 2021).*

Polyethylene properties from Dielectric Manufacturing, accessed at https://dielectricmfg.com/knowledge-base/polyethylene/ on Aug. 3, 2021 (Year: 2021).*

Melting point of silicone from Rubber Facts, accessed at https://rubberfacts.com/silicone-melting-point/ on Aug. 3, 2021 (Year: 2021).*

* cited by examiner

TRACHEOSTOMA DEVICE HOLDER

CROSS REFERENCE TO RELATED APPLICATIONS

This application claims priority to International Patent Application No. PCT/SE2019/050920 filed on Sep. 26, 2019 and Swedish Patent Application No. SE 1851155-0 filed on Sep. 27, 2018, the contents of both of which are hereby incorporated by reference in their entirety.

TECHNICAL FIELD

This invention pertains in general to a tracheostoma device holder. More particularly, the present invention pertains to a tracheostoma device holder, comprising a plate for attachment over a tracheostoma via the proximal side of the plate, said plate being provided with a through hole having a tracheostoma device fitting extending distally from the plate circumferentially of said through hole. Additionally, the present invention pertains to a method for adapting such a tracheostoma device holder to its intended user.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma valve. In these situations, the valve can be arranged to remain open during breathing but can be closed to divert the airflow, through a small additional increase in exhaled air flow.

In this respect tracheostoma devices, such as filter devices, Heat and Moisture Exchange (HME), breathing protectors, and speech valves, have been developed to enable moisturizing of inhaled air, removal of small particles and bacteriological substances in said inhaled air, and providing the person with the ability to speak by closing the air passage through the tracheostoma by manual operation. As an alternative, some use a "hands free" HME (automatic speaking valve) that is activated by speaking. A hands-free HME enables laryngectomees to speak without requiring finger occlusion. The device consists of a combination of HME and an automatic speaking valve, which closes automatically, when exhaling air for speaking, enabling the pulmonary air to be diverted through the voice prosthesis into the esophagus. It reopens automatically, when exhalation decreases.

These tracheostoma devices are held in place by a tracheostoma device holder, arranged above the tracheostoma of the person. The tracheostoma device holder is normally attached to the skin of the person by a plaster, having an adhesive surface on the side of the plaster intended to be directed towards the person using it. Either, the tracheostoma device holder is welded to the plaster, or the tracheostoma device holder is arranged on an adhesive surface on the side of the plaster intended to be directed outwards from the person using it. On the skin adhesive surface a coveting sheet may be applied, which is removed just before application of the tracheostoma device holder. The covering sheet facilitates transportation, and maintains skin adhesive ability of the skin adhesive surface.

There is however a problem associated with the application of the tracheostoma device holder after the removal of the covering sheet, since the neck of the person receiving the tracheostoma device holder by no means is planar. It is difficult to adhere the tracheostoma device holder in the pit in between the sternocleidomastoid muscles, at persons with sunken stomas, i.e. stomas that somewhat has sunken into the neck of the person, since the adhesive surface of the tracheostoma device holder inevitably will adhere to the walls of the pit before reaching the bottom of the pit with the central portion of the system. Sunken stomas are very frequent in the group of persons not having the two vertical sternocleidomastoid muscles on the neck cut during laryngectomy. Further more, a bad fit between the non-planar surface of the neck and the adhesive surface of the tracheostoma device holder may lead to leakages between the neck and said adhesive surface, since the force distribution over the plate will be uneven with local areas being more exposed than others, thereby causing a loss of speaking pressure. The force from the speaking pressure, especially during use of automatic speaking valves when the user does not hinder the tracheostoma device to move forward by finger occlusion, often leads to premature leakage.

Furthermore, in many hospitals the surgical steps during laryngectomy are adapted for creating stomas of substantially planar natures, to comply with the tracheostoma device holder system presently on the market. This adaptation includes the cutting of the two vertical sternocleidomastoid muscles on the neck.

Hence, an improved tracheostoma device holder would be advantageous, and in particular a tracheostoma device holder allowing for convenient application of the tracheostoma device holder with improved positioning ability, while simultaneously decreasing the risk of loosening of skin adhesion close to the tracheostoma, also in persons with sunken tracheostomas, thus keeping speech pressure at a convenient level, as well as making up for irregularities in skin shape adjacent the stoma.

SUMMARY

Accordingly, the present invention preferably seeks to mitigate, alleviate or eliminate one or more of the above-identified deficiencies and disadvantages, singly or in any combination, and solves at least the above mentioned problems by providing a tracheostoma device holder for holding a tracheostoma device superimposed of a tracheostoma of a person, said tracheostoma device holder comprising a plate for attachment over a tracheostoma via proximal side thereof, said plate being provided with a through hole; a tracheostoma device fitting arranged superimposed the through hole, said tracheostoma device fitting extending distally from a distal side of the plate; wherein the plate comprises a disc of a thermoplastic material enclosed by a surrounding disc material.

A method for adaptation of such tracheostoma holding device is also provided for the same reasons.

Thereby, a tracheostoma device holder which can become suitable for a wider range of stoma shapes, as well as able to follow the shape of stoma of a patient more closely, is provided.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a tracheostoma device holder, for holding a tracheostoma device, such as a tracheostoma valve, over the stoma of a person. A tracheostoma device may in this context be a HME, speech valve, etc.

Figure 1A:
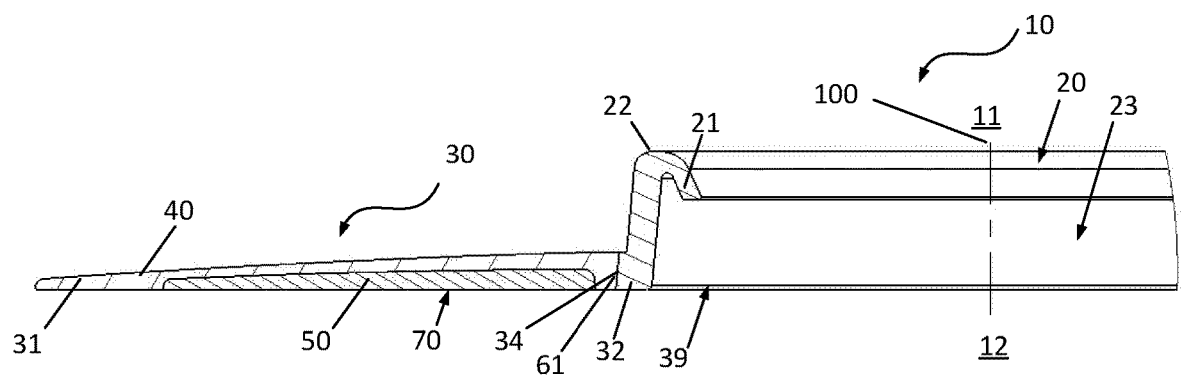
FIG. 1a is a cross-section view of a tracheostoma device holder according to an embodiment of the present invention.

FIG. 1a discloses a cross-section view of a tracheostoma device holder 10 for holding a tracheostoma device superimposed of a tracheostoma of a person, said tracheostoma device holder 10 comprising a plate 30 for attachment over the tracheostoma via a proximal side thereof, said plate 30 being provided with a through hole 39.

The tracheostoma device holder 10 further comprises a tracheostoma device fitting 20 extending distally from a distal side of the plate 30. The tracheostoma device fitting is preferably a tubular tracheostoma device fitting 20. The tracheostoma device fitting 20 comprises a through passage 23, extending through the tracheostoma device holder 10. The through passage 23 of the tracheostoma device fitting 20 is superimposed the through hole 39 of the plate 30, so as to form a distal opening 11 communicating with a proximal opening 12 in the tracheostoma device holder 10. Preferably, the aperture formed by the tubular tracheostoma device fitting 20 and said through hole 39 being provided in the plate 30 coincide about an axis 100 of the through hole 39.

The tracheostoma device holder 10 thus comprises a proximal end and a distal end. In this context proximal refers to a position or direction towards the stoma, i.e. towards the user of the tracheostoma device holder 10, whilst distal refers to a position or direction away from the stoma, i.e. away from the user of the tracheostoma device holder 10. Lateral refers to a position or direction radially away from the axis 100, whilst central refers to a position or direction towards the central axis 100. The axis 100 extends in a distal-proximal direction through the tracheostoma device holder 10. With advantage said axis 100 may coincide with a central axis of said tracheostoma device holder 10.

The tubular tracheostoma device fitting 20 is disposed circumferentially of the through hole 39, in the form of for example a cylindrical sleeve. Thus, the tracheostoma device fitting 20 extends distally from the plate 30 circumferentially of said through hole 39. The plate 30 will extend mainly laterally as a flange from the tubular tracheostoma device fitting 20, in relation to the axis 100 of the through hole 39. Similarly, the tubular tracheostoma device fitting 20 extends axially and distally from the plate 30, in accordance with above.

Referring again to FIG. 1a, the plate 30 may be of a substantially circular shape, with the through hole 39 extending through the center of said plate. The plate 30 may also have other shapes, such as polygonal or flower-shape.

Figure 2:
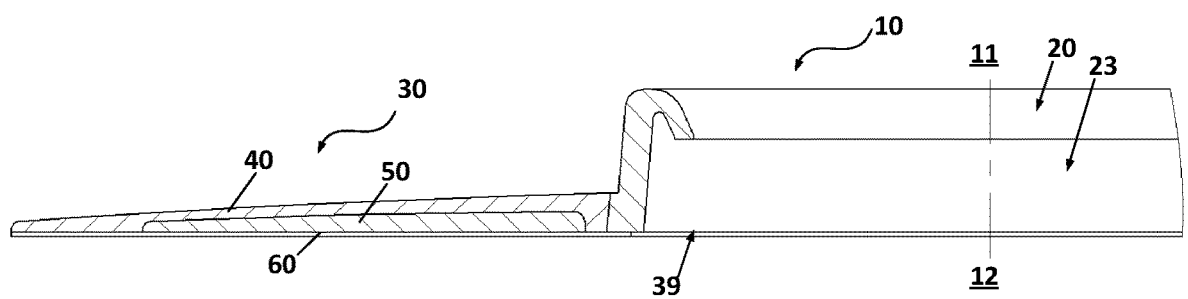
FIG. 2 is a cross-section view of a tracheostoma device holder according to an embodiment of the present invention.

According to one embodiment, as illustrated in FIG. 2, the plate 30 comprises a disc of thermoplastic material 50 enclosed at least laterally by a surrounding plate material 40. Accordingly, the plate 30 comprises at least two different materials. The plate material 40 has a melting point which is different from a melting point of the disc 50 of thermoplastic material. Centrally, the disc of thermoplastic material 50 adjoins the tracheostoma device fitting 20.

When the disc 50 is heated to its melting point, it may be possible to mold the disc 50 and thereby adapting the surface of the material to an anatomic shape of a person wearing the tracheostoma device holder 100. The molding of the disc 50 allows for forming of the plate 30 in shapes which more closely follow the shape of the stoma of a patient. By providing a plate 30 which comprises at least two materials with different melting points, it is possible to allow only a part of the plate 30 to be moldable when the plate 30 is heated to a certain temperature. The part of the plate 30 that has the lowest melting point will accordingly allow molding when the disc 50 has been heated to its melting point. At the same time, the other part, with the higher melting point, will not be melted. Thereby, it is possible to set some restriction for the moldable part, as the part of the plate 30 with the higher melting temperature may limit the possibilities of how the moldable material of the plate 30 may be formed and may also prevent it from flowing freely. Accordingly, it is possible to more accurately control the application of the tracheostoma device holder 10 and a tracheostoma device holder 10 with improved positioning ability is achieved.

According to one embodiment, as illustrated in FIG. 1a, the plate 30 comprises a disc 50 of a thermoplastic material enclosed at least centrally and laterally by a surrounding plate material 40. Accordingly, the plate 30 comprises at least two different materials, wherein the disc 50 of thermoplastic material is enclosed in both central and lateral directions by the surrounding plate material 40. The plate material 40 has a melting point which is different from a melting point of the disc 50 of thermoplastic material.

In an advantageous embodiment, the melting point of the plate material 40 is higher than the melting point of the disc 50. Thus, the surrounding plate material 40 will maintain its substantial spatial shape when the disc 50 is in a moldable state. Thereby, the surrounding plate material 40 may constitute a barrier to the disc 50, which will prevent the disc 50 from flowing beyond this barrier and then also jeopardizing the thickness of the disc, whereby force distribution again may vary over the disc 50.

The disc 50 may have a melting/softening temperature allowing for molding according to the local anatomic shape of the person through direct contact between the plate 30 and the skin of the person. Such thermoplastic may suitably be a polyester based thermoplastic, such as a polycaprolactone (PCL) based thermoplastic. Polycaprolactone is a biodegradable polyester with a low melting point of about 60° C. Once softened, it can be molded by hand in the proper shape. If the temperature of an outer layer decreases, it becomes non-sticky, but still pliable and moldable.

With reference to FIG. 1*a*, the disc of thermoplastic material 50 may be enclosed centrally and laterally by the surrounding plate material 40. Accordingly, the disc of thermoplastic material 50 may be encapsulated by the surrounding plate material 40 inwardly and outwardly, preventing it to flow beyond the surrounding plate material 40 and too far in any lateral or central direction. It is thereby made possible to prevent the disc of thermoplastic material 50 from flowing freely, potentially into the lumen of the adhesive, when in a moldable state. The disc of the thermoplastic material 50 may be prevented to flow into areas that should be avoided and where the disc of thermoplastic material 50 should not be located. Hence a more secure tracheostoma device holder 10 is provided, which follow the shape of a stoma of a patient more closely is provided.

In one embodiment, the disc of thermoplastic material 50 is further enclosed distally by the surrounding plate material 40. This may prevent the disc of thermoplastic material 50 to "escape" out of the plate 30 in a distal direction and may assure that the disc 50 stays within the plate 30. Hence, a tracheostoma device holder 10 with improved positioning ability, while simultaneously keeping the disc 50 in place is provided. By enclosing the disc 50 of thermoplastic material distally, the placing of the device may be facilitated as the sticky thermoplastic material 50 will be prevented from being exposed, which may facilitate application of the tracheostoma device holder 10. Furthermore, when the tracheostoma device holder 10 is placed over the stoma, the device may be more esthetically appealing as the surface of the plate 30 is of one coherent material. The distal plate material 40 may also prevent non-appealing fingerprints on the thermoplastic material.

The surrounding plate material 40 of the plate 30 may be made of a flexible and elastic material. The flexible and elastic material may not be heat formable at comfortably low temperatures. Example of such a material is e.g. thermoplastic materials, such as a thermoplastic elastomer (TPE). By providing the surrounding plate material 40 of the plate 30 in a flexible and elastic material, it allows for the whole plate 30 to more closely follow the shape of the stoma. Notably, the material may be so flexible that this can be achieved independently of the shape of the stoma of the patient, whereby a tracheostoma device holder 10 which is suitable for a wide range of shapes of stoma is achieved. The flexible material also reduces the risk for leakage and/or perceived discomfort of the patient by allowing for a softer material which closely follows the stoma.

According to one embodiment, the plate material 40 may be an injection molded part. Tracheostoma device holders 10 according to this embodiment are illustrated in FIGS. 1*a*, 1*b*, 2 and 4. These tracheostoma device holders 10 may be advantageous when it is desired that the shape and the form of the plate material 40 is the same and consistent in the tracheostoma device holders 10. Furthermore, this plate material 40 may be cost efficient to manufacture.

Figure 5:
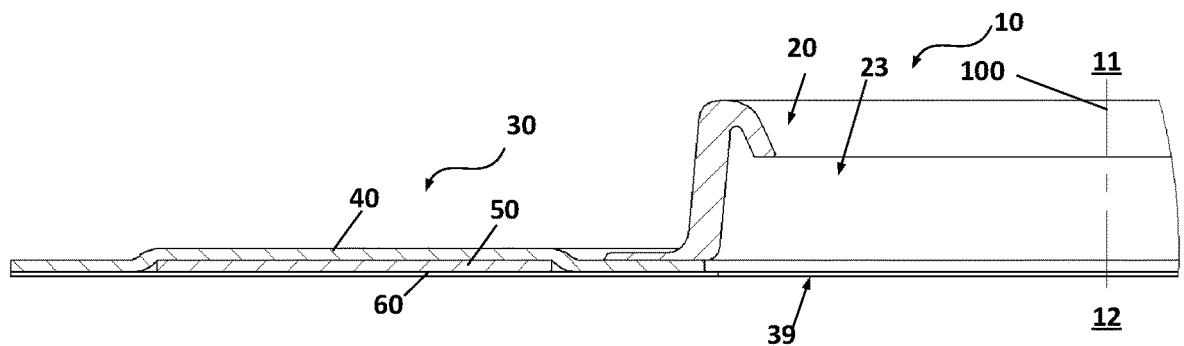
FIG. 5 is a cross-section view of a tracheostoma device holder according to an embodiment of the present invention.

According to another embodiment, the plate material 40 may be a film material. The film material may be arranged to be provided distally of the disc 50, as illustrated in FIG. 5. As previously described, this may prevent the disc of thermoplastic material 50 to "escape" out of the plate 30 in a distal direction and may assure that the disc 50 stays within the plate 30. Hence, a tracheostoma device holder 10 with improved positioning ability, while simultaneously keeping the disc 50 in place is provided. By enclosing the disc 50 of thermoplastic material distally, the placing of the device may be facilitated as the sticky thermoplastic material 50 will be prevented from being exposed, which may facilitate application of the tracheostoma device holder 10. Furthermore, when the tracheostoma device holder 10 is placed over the stoma, the device may be more esthetically appealing as the surface of the plate 30 is of one coherent material. The distal plate material 40 may also prevent non-appealing fingerprints on the thermoplastic material.

Figure 6:
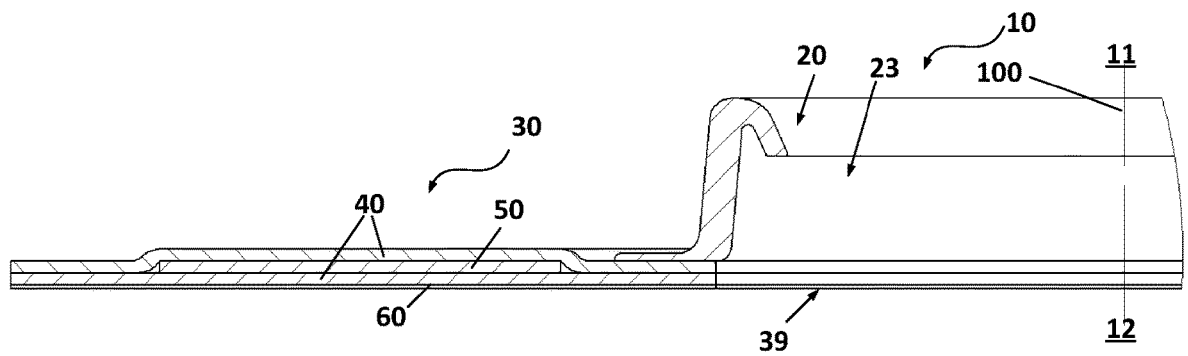
FIG. 6 is a cross-section view of a tracheostoma device holder according to an embodiment of the present invention.

Alternatively, as illustrated in FIG. 6 the film material 40 may be arranged to be provided both distally and proximally of the disc 50, such that the disc 50 is provided between two layers of film plate material 40. According to this embodiment, it is further prevented that the disc of thermoplastic material 50 "escapes" out of the plate 30 in a proximal direction and it may be assured that the disc 50 stays within the plate 30.

Figure 7:
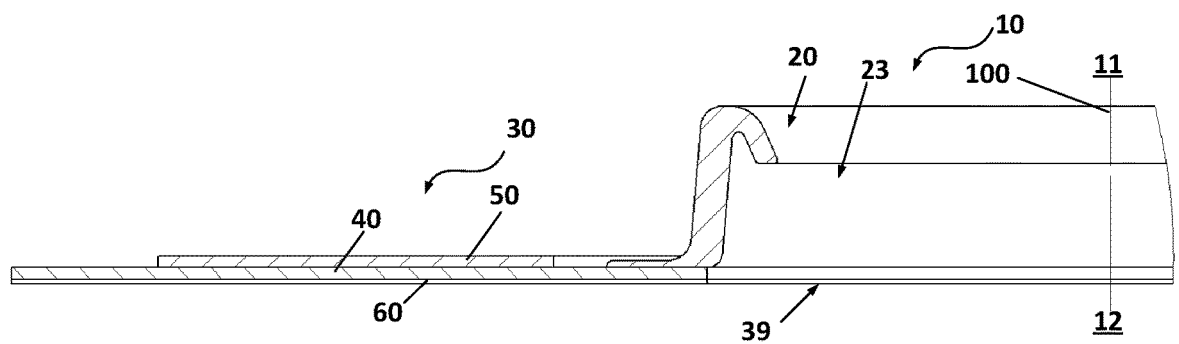
FIG. 7 is a cross-section view of a tracheostoma device holder according to an embodiment of the present invention.

In still one alternative embodiment, the film material 40 may be arranged proximally of the disc 50, as illustrated in FIG. 7. The manufacturing of this embodiment may be advantageous as the disc 50 of thermoplastic material may be provided on top of the plate material 40.

Tracheostoma device holders 10 according to these embodiments, where the plate material 40 is a film material, may be flexible and easily adjusted if the requirements for the tracheostoma device holder 10 may change.

As the plate material 40 may be either an injection molded plate or a film material plate, the tracheostoma device holder 100 may be adapted according to prevailing conditions. As the two different embodiments have different demands on, for example, manufacturing, the most suitable embodiment may be chosen.

When adapting the tracheostoma device holder 100 in correspondence with the anatomy of the neck portion in the vicinity of the tracheostoma of the person intended to use the tracheostoma device holder 100, at least the plate 30 is heated to somewhat over the melting temperature of its disc 50, i.e. approximately 65° C. in case of a PCL based thermoplastic. This is accomplished by heating the plate 30 approximately 2-5 minutes. However, the surrounding plate material 40 which has a different melting point, will not reach its melting point and accordingly, the surrounding plate material 40 will be unaffected and keep the disc 50 within the acceptable area. Accordingly, the disc of thermoplastic material will be hand moldable, but will not be able to flow away too far in any unwanted direction, such as into the lumen of the adhesive.

After the disc 50 has reached its melting temperature, the disc 50 becomes compliable, and thus hand moldable. Also, when the thermoplastic material used is a PCL based thermoplastic, the disc 50 changes in transparency from opaque to transparent. In this state, the disc 50 and thus the plate 30 is molded/shaped in accordance with the neck anatomy of the person, such that the through hole 39 is superimposed over the tracheostoma. The available molding time is normally about 2 minutes, thereafter the disc 50 turns unmoldable but still flexible. After approximately 10 minutes, the disc 50 again turns rigid, and is then ready for use. In this way, the disc 50 may be molded in correspondence with the anatomy of the neck of the user, such that it conforms with for example the two vertical sternocleidomastoid muscles, and still getting close also to sunken stomas.

Additionally, due to the change in transparency at the melting temperature of PCL based materials, not only will it be easy to know when to start the molding process, but also it will be easy to adapt the plate 30 after the anatomy of the neck, since it will be possible to see through the plate 30 and detect and make up for contour changes at the neck. The surrounding plate material 40 is preferably transparent in its normal state and will accordingly stay transparent during the whole process. Furthermore, the disc 50 may simply be remolded by reheating the plate 30 and reshaping it, if anatomy changes would occur or if it should be shaped in accordance with another user.

Figure 1B:
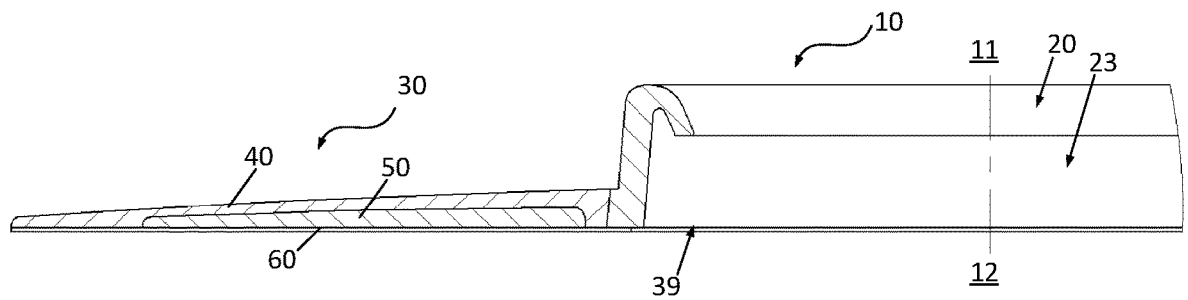
FIG. 1b is a cross-section view of a tracheostoma device holder according to an embodiment of the present invention.

As illustrated in e.g. FIG. 1b, the proximal side of the plate 30 may be provided with a coating 60 being adhesive on both sides, and at least skin adhesive on one of these. Such a coating 60 may be dimensioned in accordance with the proximal side of the plate 30, such that the interaction surface between the plate 30 and the skin may be high. By providing high formability and even force distribution a less tacky adhesive may be allowed, which may be beneficial to the user by decreasing the mechanical stress on the skin when removing the device. The adhesive may be a tape or foam tape, a sprayed or painted skin adhesive formulation.

The plate 30 may then be attached to the neck of the user, such that the through hole 39 is superimposed over the tracheostoma, and a tracheostoma device, such as a speech valve, is connected to the tracheostoma device fitting 20 in a known manner.

The adhesive coating 60 may in one exemplary embodiment further encapsulate the disc of thermoplastic material in a proximal direction.

According to one embodiment, at least the proximal side of the disc 50 may be provided with a liner 70. This allows for easier handling during molding, since it decreases the stickiness to skin. Once the plate 30 has been shaped in accordance with the contours around the stoma (and perhaps after the plate 30 has regained its rigidity after cooling) the liner is removed, and the plate attached to the neck of the patient.

Yet again referring to FIG. 1a, the tubular tracheostoma device fitting 20 may comprise a retaining lip 21 extending circumferentially from a distal zone of said fitting 20. The retaining lip 21 comprises a bent portion 22 extending proximally and laterally towards the axis 100 of the through hole of the plate. Said retaining lip 21 being adapted to receive and retain the tracheostoma device.

The receiving and the retaining of the tracheostoma device is provided by the elastic deformation of the more rigid material of the tracheostoma device fitting 20 and the bent portion 22 of the retaining lip 21. When the tracheostoma device is inserted into the fitting 20 in a distal to proximal direction along the axis 100 of the through hole 39 of the plate 30, the bent portion 22 will deform laterally towards the inner portion of the tubular tracheostoma device fitting 20. This leaves room for the tracheostoma device to pass through the retaining lip 21 and be fully inserted into the tubular tracheostoma device fitting 20.

The bent portion 22 of the retaining lip 21 then retains the tracheostoma device inside the tracheostoma device fitting 20. Due to the inwardly bent structure any distal movement of the tracheostoma device past the retaining lip will be hindered. This being due to any load on the retaining lip 21 caused by said movement will simply lead to the retaining lip 21 deforming by means of elastically bending the retaining lip 21 so as to urge the retaining lip 21 to exert a proximally directed normal force holding the tracheostoma device in place.

The retaining lip 21 thus allows for a tracheostoma device holder 10 mitigating the risk for a tracheostoma device to accidentally fall out of the tubular tracheostoma device fitting 20, when the tracheostoma device holder 10 is used by a patient.

For the tracheostoma device fitting 20 to provide a retaining lip 21 with the desired retaining properties, the fitting 20 may be provided in a more rigid material. Accordingly, the tracheostoma device fitting 20 is preferably in a more rigid material due to its required retaining properties for holding the tracheostoma device 100 in place. Thus, the more rigid material allows for a press-fit or snap-fit between the tracheostoma device fitting 20 and the inserted tracheostoma device provided by the elastic deformation of the more rigid material of the fitting 20. However, in order to provide such desired retaining properties while still providing a tracheostoma device holder 100 which is comfortable to wear for the patient, the tracheostoma device fitting 20 may be in a more rigid material than the surrounding plate material 40 of the plate 30. Accordingly, the surrounding plate material 40 is in a more flexible material than the tracheostoma device fitting 20.

A tracheostoma device holder 100 with a retaining lip solves the problem of achieving a tracheostoma device holder 100 which mitigates the risk for the tracheostoma device to accidentally fall out of the tracheostoma device fitting 20 during wearing without reducing the perceived comfort of the patient or introducing additional adhering or joining steps during manufacturing.

Figure 3:
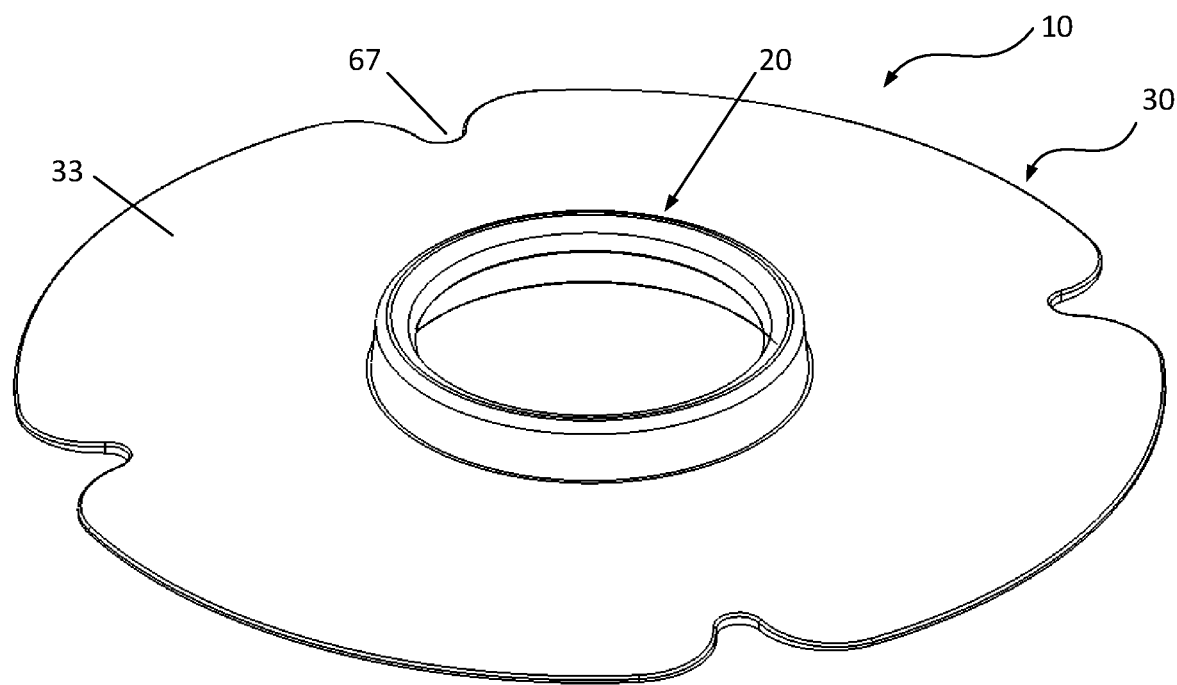
FIG. 3 is a perspective view of a tracheostoma device holder according to an embodiment of the present invention.

With reference to FIG. 3, the plate 30 further comprises a plurality of flaps 33 extending laterally from a lateral outer portion of the plate 30. The flaps 33 are preferably separated by a plurality of cut-ins 67 extending centrally towards the axis 100 from a lateral circumferential edge of the plate 30. Said flaps 33 further increase the adaptability of the plate 30 since each flap 33 may be adhered to a surface without affecting the orientation of the other flaps of the plate 30.

In a conventional plate the (partial) folding of a section of the outermost portion of the plate 30 may cause a strain propagating through the material of the plate 30 which may force other sections of said plate 30 to release from their intended position on the stoma of the patient, Said flaps 33 thus provides additional means for the plate 30 to more closely follow the shape of the stoma of a patient, furthermore they provide an improvement in the adhering properties of the plate 30. Hence, the flaps 33 provide a mean to increase the ability for the plate to follow the shape of the stoma of a patient more closely.

Again referring to FIG. 1a, the thickness of the plate 30 varies in a lateral direction, i.e. a direction substantially orthogonal to the axis 100 moving radially outwards. A central portion 32 of the plate 30 is preferably thicker than a lateral portion 31 of the plate 30. This is particularly advantageous since the thicker material of the central portion 32 allows for a stronger bond between the fitting 20 and the plate 30 due to the relatively large contact area between said fitting 20 and plate 30, while the thinner material at the lateral portion 31 makes the remaining portion of the plate 30 more flexible and formable. Additionally, a thicker central portion 32 allows for an increased force distribution around the fitting 20, upon exposure to axial or transversal forces during use. However, the lateral portion 31 is not so thin that it becomes difficult to apply or may wrinkle when the tracheostoma device holder 10 is worn by a patient.

As further depicted in FIG. 1a, an interface 34 between the plate 30 and the tubular tracheostoma device fitting 20 may be formed by a proximodistal face 61 of the plate 30 and the tubular tracheostoma device fitting 20. The proximodistal face 61 extends along the axis 100, i.e. in a proximodistal direction and abuts to the lateral face of the tubular tracheostoma device fitting 20 also extending along said axis 100, i.e. in a proximodistal direction. The interface 34 is thus a proximodistal interface 34 formed by a substantially annularly shaped boundary surrounding the tubular tracheostoma device fitting 20, extending substantially orthogonal to the skin of the user.

Due to the tracheostoma device holder 10 being susceptible to forces parallel the axis 100, which may be transferred into a shear force in the interface between the tracheostoma device fitting 20 and the plate 30, a large proximodistal interface may absorb such forces in a good way.

However, with conventional adhering operations such a proximodistal interface is difficult to achieve. Instead, the fitting is usually adhered on top of the distal surface of the plate. In such a solution little resistance is provided to shearing forces between the proximal surface of the fitting and the distal surface of the plate and the adhesion is prone to peel off. Such shearing load may induce cracks between said components which causes leakage. Thus, the orientation of the interface allows for an interface between plate and fitting which maintains structural integrity even during relatively large proximodistal loads, as well as shearing forces.

Figure 4:
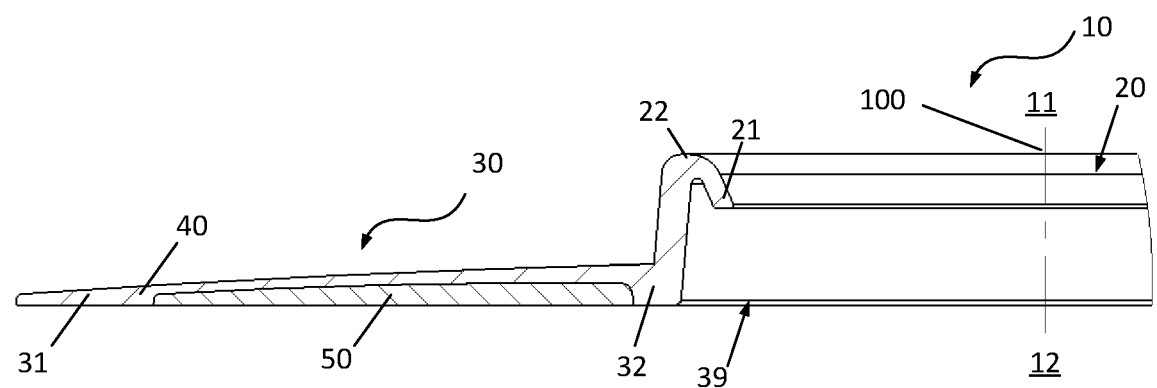
FIG. 4 is a cross-section view of a tracheostoma device holder according to an embodiment of the present invention.

According to an alternative embodiment, as illustrated in FIG. 4, the surrounding plate material 40 and the tracheostoma device fitting 20 is manufactured as one integral and monolithic body. Due to this embodiment, the production process is simplified as the two parts may be manufactured together in one process. The number of production steps is reduced, as the two parts do not have to be joined together and only one material for both the tracheostoma device fitting 20 and the surrounding plate material 40 has to be chosen. Furthermore, by eliminating the interface between the tracheostoma device fitting 20 and the surrounding plate material 40, there may be less risk of the interface between the two parts to break, as there will not exist an interface.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma device holder for holding a tracheostoma device superimposed of a tracheostoma of a person, the tracheostoma device holder comprising:
   a plate for attachment over the tracheostoma via a proximal side thereof, the plate including a through hole;
   a tracheostoma device fitting with a through passage arranged superimposed the through hole, the tracheostoma device fitting extending distally from the plate;
   the plate further including a disc of a thermoplastic material and a plate material arranged laterally of the disc;
   wherein the plate material has a melting point different from a melting point of the disc; and
   wherein the plate material is also arranged centrally of the disc and laterally of the tracheostoma device fitting such that the plate material is disposed radially between the disc and the tracheostoma device fitting.

2. The tracheostoma device holder according to claim 1, wherein the melting point of the plate material is higher than the melting point of the disc.

3. The tracheostoma device holder according to claim 1, wherein the plate material is provided distally of the disc.

4. The tracheostoma device holder according to claim 1, wherein the thermoplastic material is a polyester-based thermoplastic.

5. The tracheostoma device holder according to claim 1, wherein the thermoplastic material is a polycaprolactone (PCL)-based thermoplastic.

6. The tracheostoma device holder according to claim 1, wherein:
   the plate material is composed of a flexible and elastic material; and
   the plate material includes a thermoplastic elastomer.

7. The tracheostoma device holder according to claim 1, wherein:
   at least the proximal side of the plate includes a skin adhesive;
   the skin adhesive is configured as at least one of a tape, a foam tape, a sprayed skin adhesive formulation, and a painted skin adhesive formulation; and
   the at least one of the tape, the foam tape, the sprayed skin adhesive formulation, and the painted skin adhesive formulation is adhesive on both sides and at least one of the sides includes the skin adhesive such that the proximal side of the plate is skin adhesive.

8. The tracheostoma device holder according to claim 1, wherein the plate material is a more flexible material than a material of the tracheostoma device fitting.

9. The tracheostoma device holder according to claim 1, wherein the plate material and the tracheostoma device fitting are structured as one integral and monolithic body.

10. The tracheostoma device holder according to claim 1, wherein a thickness of the plate decreases in a central to lateral direction.

11. The tracheostoma device holder according to claim 1, wherein a lateral portion of the plate includes a plurality of flaps.

12. The tracheostoma device holder according to claim 1, wherein a thickness of the plate continuously decreases in a radially outward direction.

13. The tracheostoma device holder according to claim 1, wherein:
the plate material includes a groove disposed in a proximal side surface of the plate material; and
the disc is arranged in the groove.

14. The tracheostoma device holder according to claim 13, further comprising a skin adhesive disposed on the proximal side surface of the plate material and a proximal side surface of the disc.

15. The tracheostoma device holder according to claim 1, wherein the tracheostoma device fitting includes:
a main portion defining the through passage;
a retaining lip disposed at least partially within the through passage and extending toward the through hole; and
a bent portion connecting a distal end of the main portion and the retaining lip.

16. The tracheostoma device holder according to claim 1, wherein the tracheostoma device fitting, the plate material, and the disc are structured as separate, independent components.

17. The tracheostoma device holder according to claim 1, wherein the plate and the tracheostoma device fitting are coupled to one another along an interface defined by a radially inward facing surface of the plate and a radially outward facing surface of the tracheostoma device fitting.

18. A method for adapting a tracheostoma device holder according to claim 1, the method comprising:
heating the plate over the melting temperature of the disc of the thermoplastic material such that the disc becomes compliable and hand moldable;
applying the proximal side of the plate onto a neck of a person such that the through hole is superimposed over the tracheostoma;
shaping the disc in accordance with a neck anatomy of the person; and
at least one of actively and passively cooling the plate below the melting temperature of the disc.

19. A tracheostoma device holder for holding a tracheostoma device, comprising:
a plate for attachment over a tracheostoma, the plate including a through hole and a groove, the groove disposed in a surface of the plate and extending around the through hole;
a tracheostoma device fitting coupled to the plate and extending in an axial direction of the through hole, the tracheostoma device fitting including a through passage extending to the through hole;
a disc arranged in the groove of the plate; and
wherein the plate is composed of a plate material, the disc is composed of a disc material, and a melting point of the plate material is different than a melting point of the disc material.

20. A tracheostoma device holder for holding a tracheostoma device, comprising:
a plate for attachment over a tracheostoma, the plate including a through hole;
a tracheostoma device fitting coupled to the plate and extending in an axial direction of the through hole, the tracheostoma device fitting including:
a main portion defining a through passage extending to the through hole;
a retaining lip disposed at least partially within the through passage and extending toward the through hole;
a bent portion connecting a distal end of the main portion and the retaining lip;
a disc connected to the plate;
wherein the plate is composed of a plate material, the disc is composed of a disc material, and a melting point of the plate material is different than a melting point of the disc material; and
further comprising a skin adhesive disposed on a proximal side surface of the plate material and a proximal side surface of the disc.

* * * * *